US011633754B2

(12) United States Patent
Wang (10) Patent No.: US 11,633,754 B2
(45) Date of Patent: Apr. 25, 2023

(54) FRAGRANCE ATOMIZATION AND DIFFUSION DEVICE CONVENIENT FOR REPLACING A FRAGRANCE LIQUID CONTAINER

(71) Applicant: Hangzhou Chisong Optoelectric Technology Co., Ltd., Zhejiang (CN)

(72) Inventor: Qing Wang, Zhejiang (CN)

(73) Assignee: Hangzhou Chisong Optoelectric Technology Co., Ltd., Hangzhou (CN)

(*) Notice: Subject to any disclaimer, the term of this patent is extended or adjusted under 35 U.S.C. 154(b) by 204 days.

(21) Appl. No.: 17/346,182

(22) Filed: Jun. 11, 2021

(65) Prior Publication Data

US 2022/0219190 A1 Jul. 14, 2022

(30) Foreign Application Priority Data

Jan. 9, 2021 (CN) .......................... 202110027078.2

(51) Int. Cl.
*B05B 15/65* (2018.01)
*A61L 9/14* (2006.01)
(Continued)

(52) U.S. Cl.
CPC ............... *B05B 15/65* (2018.02); *A61L 9/14* (2013.01); *B05B 7/0012* (2013.01); *B05B 7/2424* (2013.01); *A61L 2209/133* (2013.01)

(58) Field of Classification Search
CPC ..... B05B 15/65; B05B 7/0012; B05B 7/2424; A61L 9/14; A61L 2209/133
(Continued)

(56) References Cited

U.S. PATENT DOCUMENTS

2007/0095942 A1\* 5/2007 Ray ...................... B05B 7/2456
239/433
2016/0367716 A1\* 12/2016 Conroy .................... A61L 9/14
(Continued)

FOREIGN PATENT DOCUMENTS

CN 108105711 A 6/2018
CN 105964444 B 8/2018
(Continued)

OTHER PUBLICATIONS

European Search Report of European Patent Application No. 21180532.0 dated Dec. 13, 2021.

*Primary Examiner* — Steven J Ganey (57) ABSTRACT

The present application relates to a fragrance atomization and diffusion device convenient for replacing a fragrance liquid container. The fragrance atomization and diffusion device convenient for replacing a fragrance liquid container comprises a housing, an atomization mechanism, a bottom cover and a top cover respectively located at two ends of the housing and enclosing a chamber, a bracket fixedly mounted within the chamber, a gas supply assembly and a power supply assembly, the atomization mechanism, the gas supply assembly and the power supply assembly each mounted at the bracket; the bracket is provided along the vertical direction with a mount cavity for mounting the atomization mechanism, an end of which extends through the top cover; and the atomization mechanism comprises an atomization head and a liquid storage bottle connected to the atomization head. The present application has the advantage of convenient addition of a fragrance liquid.

10 Claims, 5 Drawing Sheets

(51) Int. Cl.
 *B05B 7/00* (2006.01)
 *B05B 7/24* (2006.01)
(58) Field of Classification Search
 USPC ................ 239/124, 337, 340, 369, 433, 434
 See application file for complete search history.

(56) References Cited

U.S. PATENT DOCUMENTS

| | | | |
|---|---|---|---|
| 2020/0139387 A1 | 5/2020 | Song | |
| 2020/0254131 A1 | 8/2020 | Sevy | |
| 2021/0046256 A1* | 2/2021 | Hoffman | ............. B05B 17/0676 |
| 2022/0088257 A1* | 3/2022 | Lee | ....................... B05B 7/2424 |

FOREIGN PATENT DOCUMENTS

| | | |
|---|---|---|
| CN | 210904257 U | 7/2020 |
| CN | 211613203 U | 10/2020 |
| CN | 112023105 A | 12/2020 |
| CN | 214286072 U | 9/2021 |
| WO | 2020119124 A1 | 6/2020 |

* cited by examiner

FRAGRANCE ATOMIZATION AND DIFFUSION DEVICE CONVENIENT FOR REPLACING A FRAGRANCE LIQUID CONTAINER

CROSS-REFERENCE TO RELATED APPLICATION

The present application claims the priority of China application No. 202110027078.2, filed on Jan. 9, 2021. The entirety of the above-mentioned patent application is incorporated by reference herein and made a part of this specification.

BACKGROUND

Technical Field

The present application relates to a fragrance atomization and diffusion device convenient for replacing a fragrance liquid container.

Description of Related Art

As with the development of society and the improvement of people's living standards, cars have become more and more important means of transportation for people to travel, and the comfort of cars has become a point of more concern for people. In order to improve the air environment in the car, people often place car accessories that can emit fragrance in the car, such as an aromatherapy box, a fragrance box and like.

In the related technology of a fragrance use equipment, for example, a liquid molecular ion atomizer comprises a columnar housing, a top cover and a bottom cover connected to the housing, a support frame provided within the housing, a storage bottle and a gas pump, and the housing and the support frame are positioned by a lock block on the bottom cover. The support frame is provided with an atomization structure that comprises an atomization structure body, an air inlet nozzle and a liquid inlet nozzle. The liquid inlet nozzle passes through the support frame and is communicated with the storage bottle. One end of the air inlet nozzle is connected to the gas pump and the other end thereof is inclined upwards and passes through the atomization structure body. The liquid inlet nozzle is provided below the air inlet nozzle. In this technical solution, when the liquid is atomized, the liquid in the storage bottle is firstly pressed into the atomization structure body by the gas pump, and the liquid sprayed by the liquid inlet nozzle is dispersed by the high airflow of the air inlet nozzle, thereby completing the atomization.

Regarding the above-mentioned related technologies, the applicant believes that the fragrance liquid in the related technology needs to be replaced after it is used. In this technical solution, the replacement of the fragrance liquid needs to firstly open the housing through the lock block and take out the inside integral part, and then separately remove the storage bottle, namely the liquid storage bottle, in the inside integral part for replacement, and such a replacement method is more complicated.

SUMMARY

In order to facilitate the addition of a fragrance liquid, the present application provides a fragrance atomization and diffusion device convenient for replacing a fragrance liquid container.

The fragrance atomization and diffusion device convenient for replacing a fragrance liquid container provided by the present application adopts the following technical solutions.

A fragrance atomization and diffusion device convenient for replacing a fragrance liquid container, comprises a housing, an atomization mechanism, a bottom cover and a top cover respectively located at two ends of the housing and enclosing a chamber, a bracket fixedly mounted within the chamber, a gas supply assembly and a power supply assembly, the atomization mechanism, the gas supply assembly and the power supply assembly each mounted at the bracket; the bracket is provided along the vertical direction with a mount cavity for mounting the atomization mechanism, an end of the mount cavity is closed by the top cover, the top cover is provided with a plug port communicated with the mount cavity, and the atomization mechanism comprises an atomization head and a liquid storage bottle connected to the atomization head;

the bracket is provided with a positioning mechanism for positioning the atomization mechanism, and the positioning mechanism comprises a sliding member for abutting against the atomization mechanism and a positioning assembly for positioning the sliding member, wherein the sliding member is mounted slidably along the axial direction of the mount cavity to the bracket, and the positioning assembly comprises a door lock switch and a buckle joint that engages or disengages with the door lock switch as the sliding member moves up and down, and when the buckle joint and the door lock switch disengage, the atomization head protrudes out of a mounting port;

an atomization cavity is provided within the atomization head, the upper end of the atomization cavity is provided with a fog hole communicated with the outside of the atomization head, the inner wall of the atomization cavity is respectively provided with a gas intake nozzle communicated with the outside of the atomization head and with a liquid intake nozzle communicated with the liquid storage bottle, and when the buckle joint and the door lock switch engage, the gas intake nozzle is communicated with the gas supply assembly.

By adopting the above technical solution, when atomizing the fragrance liquid, the liquid storage bottle filled with the fragrance liquid is connected to the atomization head firstly, and the liquid storage bottle along with the atomization head together is put into the mount cavity; then a downward force is applied on the atomization head so that the atomization head pushes the sliding member to slide downwards, and the force applied on the atomization head is stopped until the buckle joint engages with the door lock switch, and at this time, the atomization mechanism is mounted within the mount cavity. When it needs to be replaced, the atomization head is pressed downwards to release the engagement of the buckle joint with the door lock switch, and the resetting force of the door lock switch pushes the atomization head out of the upper end opening of the mount cavity, and at this time, an operator can hold the atomization head to apply a force to take out the atomization mechanism for replacement. Through the provision of the positioning mechanism, it is convenient to position the atomization head, and when replacing the liquid storage bottle or filling the fragrance liquid, one only need to press the atomization head again to make the atomization head with the liquid storage bottle pop out of the mount cavity for easy replacement.

Preferably, the sliding member is provided in a circular shape, and there are at least two groups of the positioning assemblies circumferentially arranged along the sliding member.

By adopting the above technical solution, through the provision of at least two groups of the positioning assemblies, the balance and stability of the sliding member positioning are improved.

Preferably, the positioning mechanism further comprises a limiting assembly for limiting the sliding member, there are provided at least one group of the limiting assembly and at least one group of the positioning assembly, each limiting assembly corresponds to one positioning assembly, the limiting assembly comprises a slider and a sliding channel, the sliding channel is provided along the sliding direction of the sliding member with a sliding groove, and the slider is located within the sliding groove and slidably connected to the sliding groove.

By adopting the above technical solution, through the provision of the limiting assembly, when the sliding member slides, the slider slides in the sliding groove provided in the sliding channel to guide the sliding of the sliding member, so that the sliding member can only slide along the vertical direction, which improves the stability of the sliding of the sliding member.

Preferably, the positioning mechanism further comprises a resetting assembly for driving the sliding member to be reset, there are provided at least one group of the resetting assembly and at least one group of the positioning assembly, each resetting assembly corresponds to one positioning assembly, the resetting assembly comprises a resetting spring for driving the sliding member to move towards the opening direction of the mount cavity and a guide rod fixedly connected to the bracket, and the resetting spring is sleeved on the guide rod and the upper end thereof abuts against the sliding member.

By adopting the above technical solution, through the provision of the resetting assembly, when the sliding member slides downwards to the locked position, the resetting spring is in a compressed state, and when the engagement of the buckle joint with the door lock switch are released, the resetting spring releases the elastic force and pushes the sliding member so as to make the atomization head pop out of the mount cavity, which facilitates taking of the atomization head after unlocking.

Preferably, the atomization head is provided along the radial direction thereof with at least one limit rib, the top cover is provided at the opening of the mount cavity with a limit rib groove communicated with the upper end face of the top cover, the position and the number of which corresponds to those of the limit ribs, and when the limit rib is located within the corresponding limit rib groove, the gas intake nozzle is communicated with the gas supply assembly.

By adopting the above technical solution, through the cooperating provision of the limit rib and the limit rib groove on the top cover, when installing the atomization head, the atomization head can slide into the mount cavity only according to a specific position, which is convenient for the operator to determine the installation direction. And through the cooperation of the limit rib and the limit rib groove, when the atomization head is mounted in the mount cavity, the gas intake nozzle can always be aligned with the gas supply assembly, which improves the stability of use.

Preferably, the gas supply assembly comprises a gas pump and a gas intake nozzle, and the gas pump is communicated with the inner wall of the mount cavity through the gas intake nozzle; the atomization head is provided at the gas intake nozzle with an insert groove into which a connecting block is inserted, and a communication cavity communicated with the gas intake nozzle is provided within the connecting block; an end of the communication cavity far away from the gas intake nozzle extends the connecting block, and an end of the connecting block towards the mount cavity protrudes out of the side wall of the atomization head and abuts against the inner wall of the mount cavity.

By adopting the above technical solution, through the provision of the insert groove and the connecting block, the sealing between the gas intake nozzle and the mount cavity is improved, and the gas intake efficiency of the gas supply assembly to the atomization cavity is improved; and the friction between the atomization head and the inner wall of the mount cavity is increased through the connecting block, thereby improving the stability of the atomization head in the mount cavity.

Preferably, the inner wall of the mount cavity is provided along the radial direction thereof with a limit groove, and the limit groove extends along the sliding direction of the atomization head to the opening of the top cover.

By adopting the above technical solution, through the provision of a connection groove, when the atomization head slides within the mount cavity, one end of the connecting block towards the inner wall of the mount cavity is located within the connection groove and is slidably connected to the connection groove so that the sliding of the connecting block is guided, which improves the stability of the sliding of the atomization head during installation, and reduces the probability of the operator not aligning the atomization head with the gas supply assembly, making it easier to install.

Preferably, the connecting block is made of elastic material and abuts against the limit groove.

By adopting the above technical solution, the provision of elastic material and the abutting structure can ensure airtightness, and at the same time, a good resistance can be formed through the connecting block, so that when the atomization mechanism is mounted in the mount cavity, a good fixing effect is achieved.

Preferably, the positioning assembly further comprises a door lock mount block detachably connected to the bracket and provided along the thickness direction thereof with a mount groove, and the door lock switch is inserted within the mount groove and is limited and fixed along the length direction of the door lock switch.

By adopting the above technical solution, through the provision of the door lock mount block, when the door lock switch needs to be replaced, one only need to remove the door lock mount block from the bracket, and then the door lock switch can be taken out of the door lock for replacement, which is convenient for the installation and removal of the door lock switch.

Preferably, the bracket is provided with a mount base having a bolt passed therethrough, the door lock mount block is provided along the thickness direction thereof with a deform hole, and the bolt passes through the deform hole and is threadedly connected to a side of the deform hole far away from the mount base.

By adopting the above technical solution, the door lock mount block is connected to the mount base of the bracket through the bolt, which is easy to disassemble and install. Meanwhile, through the provision of the deform hole, during normal installation, the bolt is turned until the door lock mount block abuts against the mount base, so that the installation of the door lock mount block and the door lock switch is completed. If the door lock switch and the buckle joint are engaged at this time, and if the upper end face of the atomization head is higher or lower than the upper end face of the top cover, it is necessary to continue turning of the bolt to deform the deform hole under compression, which is convenient for adjusting the position of the door lock switch.

In summary, the present application has the following beneficial effects:

1. through the provision of the positioning mechanism, it is convenient to disassemble the atomization mechanism and replace the liquid storage bottle;

2. through the provision of the limiting assembly, the stability of the sliding of the sliding member is improved;

3. through the provision of the resetting assembly, it is convenient to take the atomization head after unlocking;

4. through the cooperating provision of the limit rib and the limit groove on the top cover and the cooperating provision of the connecting block and the connection groove, it is convenient for the operator to observe the correct installation position;

5. through the provision of the door lock mount block, it is convenient to install, remove and adjust the position of the door lock switch.

DESCRIPTION OF REFERENCE SIGNS

1—bottom cover; 2—top cover; 21—limit rib groove; 22—plug port; 3—bracket; 31—mount cavity; 32—limit groove; 33—mount base; 4—housing; 5—atomization mechanism; 51—atomization head; 511—atomization cavity; 512—fog hole; 513—insert groove; 514—air intake nozzle; 515—connection groove; 5151—connection head; 5152—gas intake groove; 5153—liquid intake nozzle; 5154—liquid discharge pipe; 516—connecting block; 5161—communication cavity; 517—limit rib; 52—liquid storage bottle; 6—gas supply assembly; 61—gas pump; 62—air intake nozzle; 7—battery; 8—sliding member; 9—positioning assembly; 91—door lock switch; 911—casting; 912—inner core; 913—coupler; 914—positioning block; 92—door lock mount block; 921—mount groove; 922—positioning groove; 923—deform hole; 924—thread hole; 93—buckle joint; 10—limiting assembly; 101—slider; 102—sliding channel; 1021—sliding groove; 103—abutting block; 11—resetting assembly; 1101—resetting spring; 1102—guide rod; 1103—guide groove; 1104—limit plate; 1105—arch groove.

DESCRIPTION OF THE EMBODIMENTS

The application will be further described in detail below in conjunction with the drawings.

Figure 1:
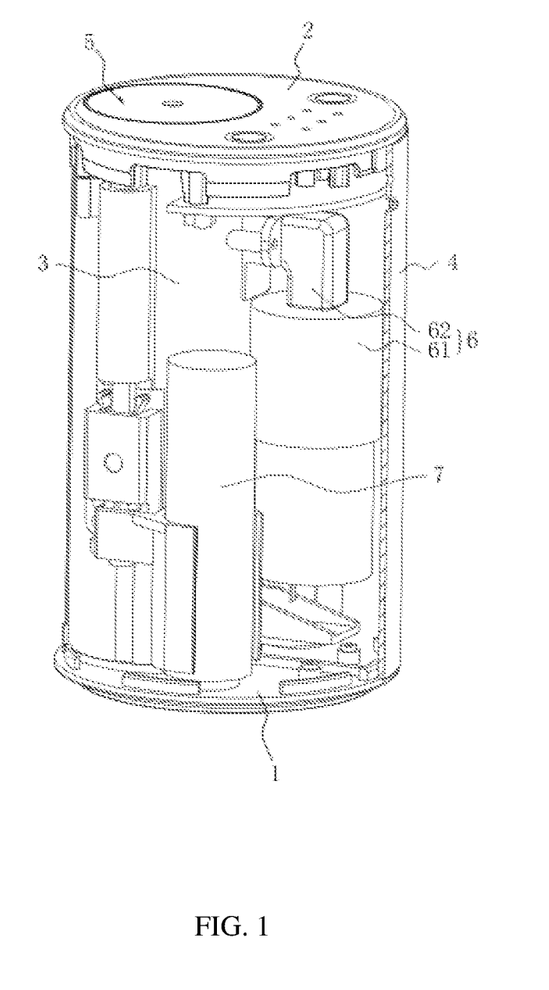
FIG. 1 is a half-sectional schematic view of the overall internal structure of a housing of the present application embodiment.

A fragrance atomization and diffusion device convenient for replacing a fragrance liquid container, as shown in FIG. 1, comprises a bottom cover 1, a top cover 2, a bracket 3, a housing 4, an atomization mechanism 5, a gas supply assembly 6 and a power supply assembly. The housing 4 is cylindrical in shape. The bottom cover 1 and the top cover 2 are respectively mounted at two ends of the housing 4. The bracket 2, the atomization mechanism 5, the gas supply assembly 6 and the power supply assembly each are mounted within a chamber surrounded by and formed by the bottom cover 1, the top cover 2 and the housing 4.

Figure 2:
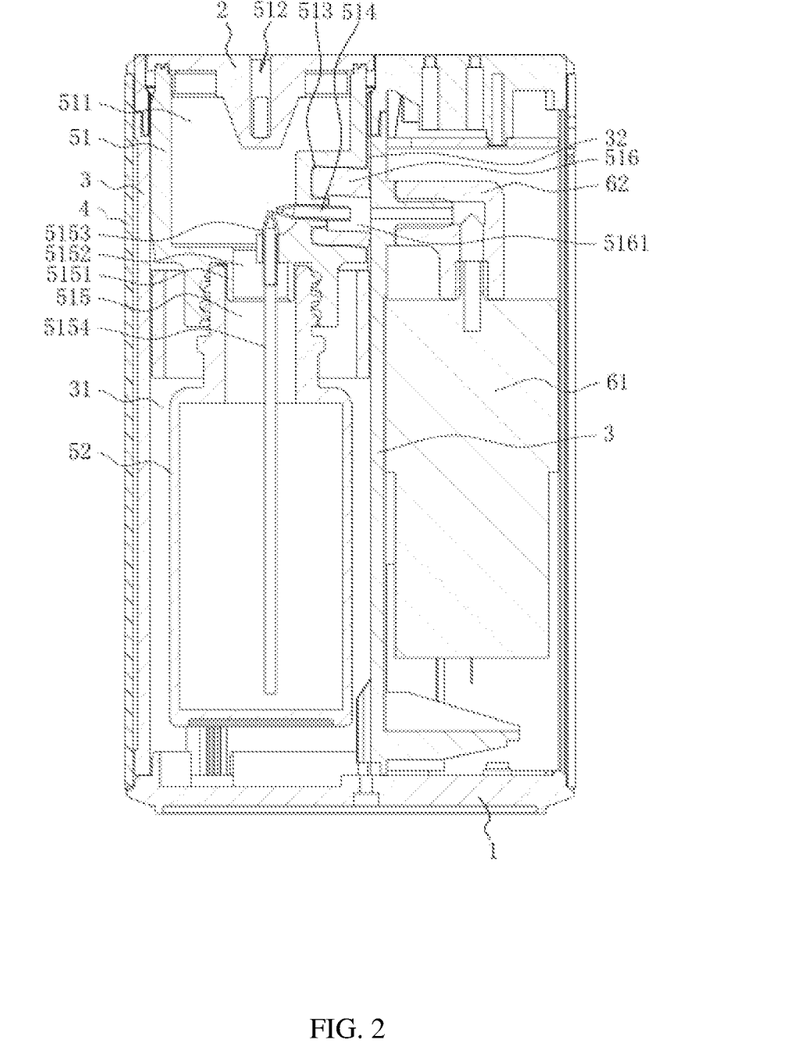
FIG. 2 is a schematic cross-sectional view of connection of an atomization mechanism and a gas supply assembly in the present application embodiment.

The bracket 3 as a whole is cylindrical in shape, and the upper and lower ends thereof are respectively connected with the bottom cover 1 and the top cover 2. Referring to FIG. 2, the bracket 3 is provided along the vertical direction with a mount cavity 31 that is cylindrical in shape and is provided coaxially to the bracket 3. An end of the mount cavity 31 is closed by the top cover 2, and the top cover 2 is provided with a plug port 22 communicated with the mount cavity 31 for inserting the atomization mechanism 5. The atomization mechanism 5 is mounted to the bracket 3 and is located within the mount cavity 31. The bracket 3 and the housing 4 are provided at intervals and form a mounting space for mounting the gas supply assembly 6 and the power supply assembly.

When atomizing the fragrance liquid, the gas supply assembly 6 injects the gas into the atomization mechanism 5, and the atomization mechanism 5 atomizes the fragrance liquid and discharges it from above.

Referring to FIG. 2, the bottom cover 1 and the top cover 2 each are detachably connected to the bracket 3 by a bolt, and the housing 4 is fixed between the bottom cover 1 and the top cover 2. When installing, the top cover 2 is connected to the bracket 3 by the bolt firstly, then the housing 4 is sleeved around the bracket 3, and finally the bottom cover 1 is connected to the bracket 3 by the bolt, so that the housing 4 is fixed.

The gas supply assembly 6 comprises a gas pump 61 and a gas intake nozzle 62. The gas intake nozzle 62 is L-shaped, the horizontal end thereof is fixedly mounted on the bracket, and the vertical end thereof is connected with the gas pump 61. The bracket 3 is provided with a passage communicated with the gas intake nozzle 62, and the other end of the passage is communicated with the mount cavity 31.

Referring to FIG. 1, the power supply assembly in this embodiment is two batteries 7, both of which are mounted on the bracket 3. The batteries 7 are electrically connected with the gas pump 61, wherein the battery 7 in this embodiment may be a rechargeable battery, and the housing 4 is provided with a charging port for charging the battery.

Referring to FIG. 2, the atomization mechanism 5 comprises an atomization head 51 and a liquid storage bottle 52.

An atomization cavity 511 is provided within the atomization head 51, and the upper end of the atomization cavity 511 is provided with a fog hole 512 communicated with the outside of the atomization head 51.

An end of the atomization cavity 511 towards the liquid storage bottle 52 is provided with a connection groove 515, through which the atomization head 51 is connected to the liquid storage bottle 52. A connection head 5151 is provided coaxially within the connection groove 515 and intergrally formed with the connection groove 515, and when the liquid storage bottle 52 is connected within the connection groove 515, the connection head 5151 is inserted into the liquid storage bottle 52.

The connection head 5151 is provided with a gas intake groove 5152 communicated with the atomization cavity 511 and the liquid storage bottle 52. A side of the connection head 5151 towards the atomization cavity 511 is provided vertically and fixedly with a liquid intake nozzle 5153 connected with and communicated with a liquid discharge pipe 5154 located at an end of the connection head 5151 towards the liquid storage bottle 52. The liquid discharge pipe 5154 extends into the liquid storage bottle 52 and extends to the body of the liquid storage bottle 52.

The side of the atomization head 51 is recessed to form an insert groove 513 into which a gas intake nozzle 514 extends, and the head of the gas intake nozzle 514 extends into the atomization cavity 511. An end of the gas intake nozzle 514 towards the atomization cavity 511 is connected at a side of the liquid intake nozzle 5153, and turns up towards an end of the liquid intake nozzle 5153, so that the gas intake nozzle 514 and the liquid intake nozzle 5153 are set at an angle.

A connecting block 516 is inserted into the insert groove 513. The connecting block 516 is made of elastic material, which may be silicone, rubber, etc. A communication cavity 5161 is provided within the connecting block 516 and extends through two ends of the connecting block 516, and one end thereof located within the insert groove 513 is docked with and communicated with the gas intake nozzle 514.

One side of the connecting block 516 is partially exposed out of the insert groove 513. The mount cavity 31 is provided along the radial direction thereof with a limit groove 32. The limit groove 32 extends along the vertical direction, so that when the atomization head 51 slides within the mount cavity 31, an end of the connecting block 516 towards the inner wall of the mount cavity 31 is located within the limit groove 32 and is slidably connected along the vertical direction to the limit groove 32, and the connecting block 516 abuts against the bottom end face of the limit groove 32, and when the mounting of atomization head 51 is completed, the communication cavity 5161 is docked with and communicated with a through hole in the bracket 3.

When the gas pump 61 supplies the gas to the atomization cavity 511 through the gas intake nozzle 62 and the gas intake nozzle 514, the gas is filled in the atomization cavity 511. By setting a gas intake rate to be greater than a gas output rate of the fog hole 512 on the atomization cavity 511, the gas pressure in the atomization cavity 511 is made higher, the gas in the atomization cavity 511 is pressed into the liquid storage bottle 52 from the gas intake groove 5152, and the liquid in the liquid storage bottle 52 is pressed into the liquid intake nozzle 5153 along the liquid discharge pipe 5154 and is sprayed out and into the atomization cavity 511, and then is dispersed and atomized by the high-speed gasflow injected by the gas intake nozzle 514, so that the atomized fragrance liquid is output from the fog hole 512.

Figure 3:
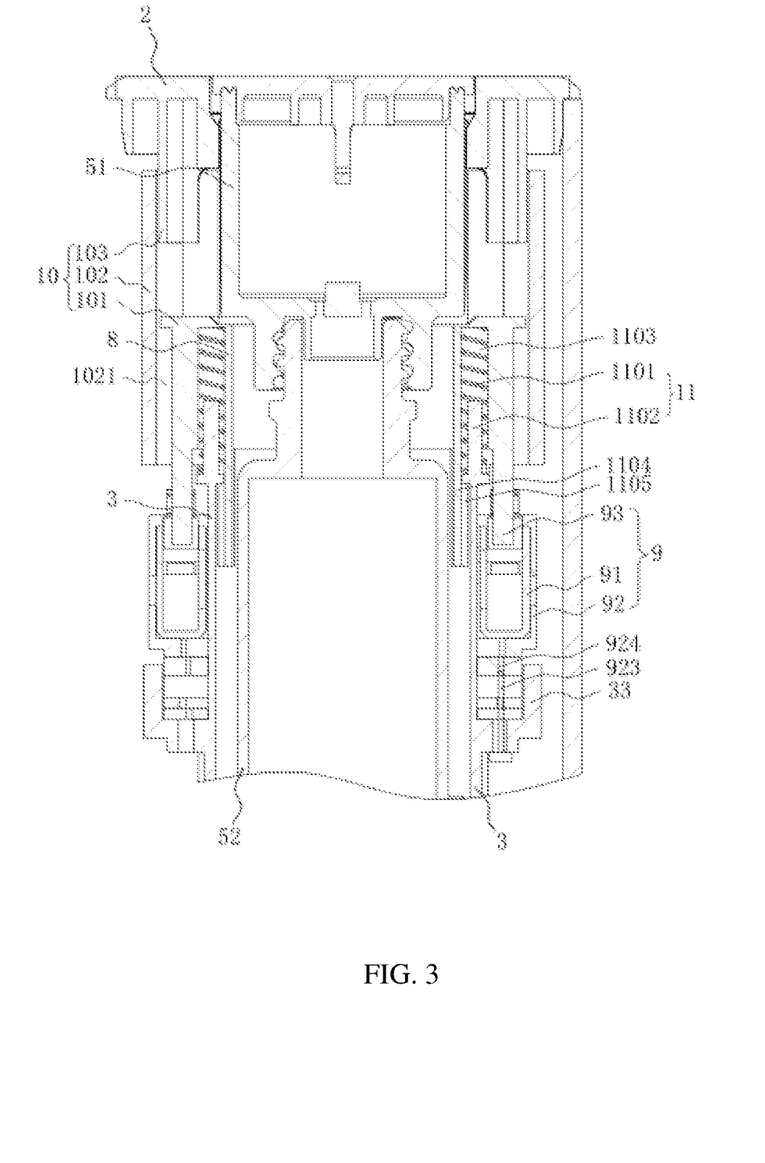
FIG. 3 is a schematic cross-sectional view of the structure of the atomization mechanism and a positioning mechanism in the present application embodiment.

Referring to FIG. 3, the bracket 3 is provided with a positioning mechanism for positioning the atomization mechanism 5. The positioning mechanism comprises a sliding member 8, a positioning assembly 9 for positioning the sliding member 8, a limiting assembly 10 for limiting the sliding of the sliding member 8, and a resetting assembly 11 for driving the sliding member 8 to be reset.

The sliding member 8 is provided in a circular shape for abutting against the bottom end of the atomization head 51, wherein the shape of the sliding member 8 is not limited to a circular shape, and may also be a circular arc shape. The sliding member 8 is slidably connected along the axial direction of the mount cavity 31 within the mount cavity 31. The inner diameter of the sliding member 8 is smaller than the outer diameter of the atomization head 51.

The limiting assembly 10, the resetting assembly 11 and the positioning assembly 9 each are provided as at least two groups. In this embodiment, for example, there are two groups of the limiting assemblies 10, two groups of the resetting assemblies 11 and two groups of the positioning assemblies 9, and each two groups are symmetrically located at two sides of the sliding member 8.

The limiting assembly 10 comprises a slider 101 provided along the radial direction of the sliding member 8 and intergrally formed with the sliding member 8, a sliding channel 102 provided along the radial direction of the bracket 3, and an abutting block 103 inserted within the sliding channel 102. The sliding channel 102 is provided along the vertical direction with a sliding groove 1021 for the slider 101 to slide. The sliding groove 1021 is provided on the inner side wall of the mount cavity 31, and the upper and lower ends of the sliding groove 1021 are communicated with the outside of the bracket 3. The slider 101 is slidably connected, along the axial direction of the mount cavity 31, within the sliding channel 102. Through the guiding by the slider 101 and the sliding groove 1021, the sliding member 8 vertically slides stably. The abutting block 103 is intergrally formed at the lower end of the top cover 2, and abuts against the upper end of the slider 101, thereby preventing the sliding member 8 from disengaging the sliding channel 102.

The positioning assembly 9 comprises a door lock switch 91, a door lock mount block 92 for mounting the door lock switch 91 on the bracket 3, and a buckle joint 93.

Figure 4:
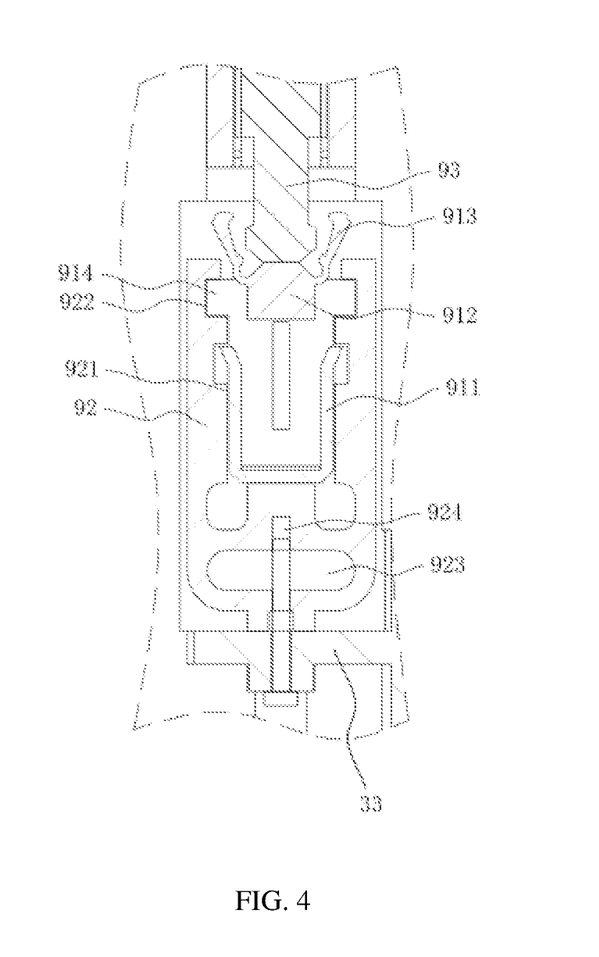
FIG. 4 is a schematic cross-sectional view of the structure of the positioning assembly in the present application embodiment.

Referring to FIG. 4, the door lock switch 91 is an existing technology, and may adopt directly such as the door lock switch 91 of the "Heying DL-100" on the market. The door lock switch 91 is used to cooperate with the buckle joint 93 to form an engagement. The door lock switch 91 mainly comprises a casting 911, an inner core 912, and two couplers 913 provided at intervals and rotatably connected to the inner core 912. When the door lock switch 91 is in the unlocked state, the two couplers 913 are in the open state and apply a force on the buckle joint 93 to make the buckle joint 93 insert into the door lock switch 91 and push the inner core 912 to slide toward the casting 911. After that, the two couplers 913 close inwards and catch the buckle joint 93, and at this time, the application of force to the buckle joint 93 is finished, and the inner core 912 is rebounded for a short distance and then is locked in the casting 911. In case of releasing the locked state, similarly, a force is applied to the buckle joint 93 to make the buckle joint 93 also push the inner core 912 into the casting 911 for a short distance, and then the buckle joint 93 is released, so that the inner core 912 is popped out of the casting 911, and the two couplers 913 are opened, releasing the locking with the buckle joint 93.

The door lock mount block 92 is provided along the thickness direction thereof with a mount groove 921 for mounting the door lock switch 91, the door lock switch 91 to be inserted within the mount groove 921. The two sides of the door lock switch 91 are respectively intergrally formed with a positioning block 914. The mount groove 921 is provided with corresponding positioning grooves 922 at two sides of the door lock switch 91, and the positioning block 914 is inserted into the positioning groove 922 so that the door lock switch 91 is limited and fixed along the length direction of the door lock mount block 92.

Referring to FIGS. 3 and 4, the buckle joint 93 is intergrally formed at an end of the slider 101 towards the door lock switch 91, and slides in the sliding groove 1021.

The lower end of the buckle joint 93 is in an umbrella shape, and when the buckle joint 93 is snapped within the door lock switch 91, it is limited and fixed along the vertical direction.

Outside of the bracket 3, it is intergrally formed with a mount base 33 for connecting the door lock mount block 92. The mount base 33 is located at the lower end of the door lock mount block 92, and has a bolt passed therethrough along the vertical direction. The lower end of the door lock mount block 92 is provided along the thickness direction thereof with a deform hole 923 that is waist-shaped in vertical section. The upper end of the deform hole 923 is provided along the vertical direction with a thread hole 924, and the lower end thereof is provided along the vertical direction with a through hole. When the door lock mount block 92 is mounted on the mount base 33, the bolt passes through the mount base 33 and the through hole, and is threadedly connected to the thread hole 924, and when the lower end of the door lock mount block 92 abuts against the mount base 33, if the position is still incorrect, the bolt is continued to be rotated, so that the deformation hole 923 is squeezed and deformed.

Referring to FIG. 3, the resetting assembly 11 comprises a resetting spring 1101 and a guide rod 1102. The slider 101 is provided along the sliding direction of the sliding member 8 with a guide groove 1103. An end of the resetting spring 1101 is located within the guide groove 1103, and the other end thereof is sleeved on the guide rod 1102 so as to position the resetting spring 1101. The lower end of the sliding member 8 is intergrally formed along the vertical direction with a limit plate 1104. The limit plate 1104 and the buckle joint 93 are provided at intervals, the limit plate 1104 is located within the mount cavity 31, and the buckle joint 93 is located within the sliding channel 102. The side of the limit plate 1104 towards the resetting spring 1101 is provided with an arch groove 1105, the bottom of which is attached to the resetting spring 1101. When the sliding member 8 slides along the vertical direction, the sliding member 8 presses the resetting spring 1101, and after the resetting spring 1101 is compressed, the sliding member 8 slides to make the guide rod 1102 to be inserted within the guide groove 1103, until the buckle joint 93 and the door lock switch 91 cooperate and complete the engagement.

Figure 5:
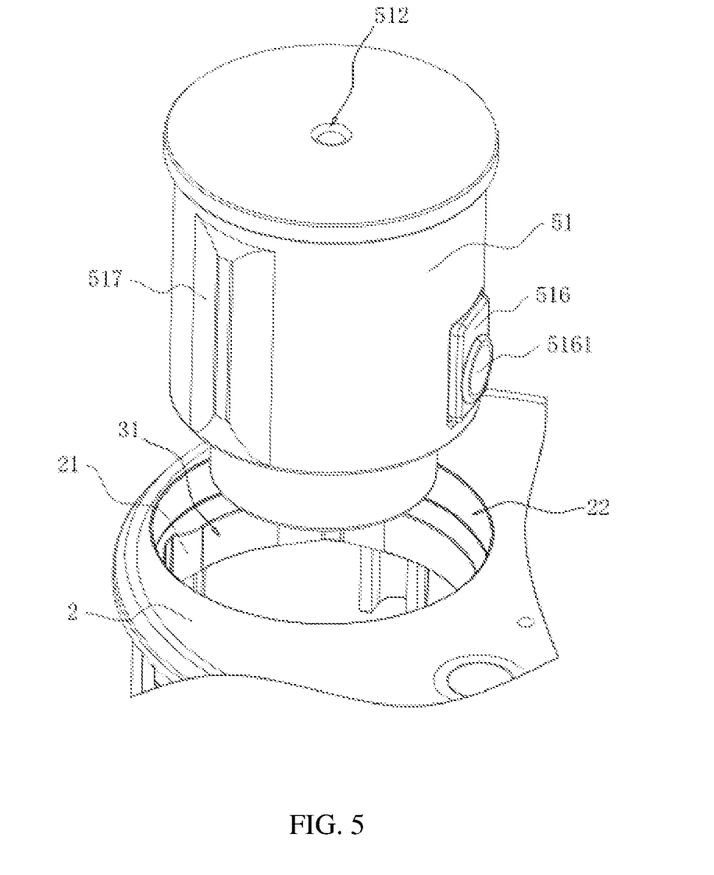
FIG. 5 is a schematic view of the structure of the separation of an atomization head and a top cover in the present application embodiment.

Referring to FIG. 5, the atomization head 51 is intergrally formed along the radial direction thereof with a plurality of limit ribs 517 circumferentially arranged along the atomization head 51. In this embodiment, taking three limit ribs 517 for example. Three limit ribs 517 are located at a side of the peripheral wall of the atomization head 51 far away from the insert groove 513. The mount cavity 31 portion of the top cover 2 is provided correspondingly with limit rib grooves 21, and when the operator installs the atomization head 51, only when all of the three limit ribs 517 are aligned with the limit rib grooves 21, the atomization head 51 can slide into the mount cavity 31, so that when installing the atomization head 51, the gas intake nozzle 514 can always be aligned with the gas intake nozzle 62.

The implementation principle of the present application embodiment is as follows.

When atomizing the fragrance liquid, the liquid storage bottle 52 filled with the fragrance liquid is connected to the atomization head 51 firstly, and the whole atomization mechanism 5 is mounted within the mount cavity 31, at this time the gas intake nozzle 514 of the atomization head 51 is aligned with and communicated with the gas supply assembly 6. The power supply assembly drives the gas pump 61 to supply the gas into the atomization cavity 511 through the gas intake nozzle 62. When the gas pressure in the atomization cavity 511 is relatively large, the gas intake groove 5152 makes the gas pressure in the liquid storage bottle 52 also increase, so that the fragrance liquid in the liquid storage bottle 52 is pressed into the liquid discharge pipe 5154, and is sprayed out of the liquid intake nozzle 5153 and into the atomization cavity 511, and the fragrance liquid is dispersed and atomized by the high-speed gasflow of the gas intake nozzle 514 while entering the atomization cavity 511, and is output from the fog hole 512 to complete the atomization of the fragrance liquid.

When installing the liquid storage bottle 52 filled with the fragrance liquid, the liquid storage bottle 52 is threadedly connected to the connection groove 515 at the lower end of the atomization head 51 firstly, and then the three limit ribs 517 are aligned with the limit rib grooves 21 in a state that the liquid storage bottle 52 faces downwards and the atomization head 51 faces upwards, and then they are placed vertically into the mount cavity 31 until the lower end of the atomization head 51 abuts against the sliding member 8. With a hard down pushing, the atomization head 51 pushes the sliding member 8 to slide downwards until the buckle joint 93 and the door lock switch 91 complete the engagement. At this time, the upper end face of the atomization head 51 is just flush with the upper end face of the top cover 2, and the atomization head 51 is limited and fixed along the vertical direction through the friction between the connecting block 516 and the bottom of the connection groove 515, thereby completing the installation of the liquid storage bottle 52.

When replacing, the atomization head 51 is pressed downwards, the buckle joint 93 is released from the engagement with the door lock switch 91, the resetting spring 1101 drives the atomization head 51 to pop out of the mount cavity 31, and the atomization head 51 is taken out so as to replace the liquid storage bottle 52.

The examples of this specific implementation manner are all preferred examples of this application, and are not intended to limit the scope of protection of this application. Therefore: all equivalent changes made in accordance with the structure, shape, and principle of this application should be covered within the scope of protection of this application.

What is claimed is:

1. A fragrance atomization and diffusion device convenient for replacing a fragrance liquid container, comprising a housing (4), an atomization mechanism (5), a bottom cover (1) and a top cover (2) respectively located at two ends of the housing (4) and enclosing a chamber, a bracket (3) fixedly mounted within the chamber, a gas supply assembly (6) and a power supply assembly, the atomization mechanism (5), the gas supply assembly (6) and the power supply assembly each mounted at the bracket (3), characterized in that: the bracket (3) is provided along the vertical direction with a mount cavity (31) for mounting the atomization mechanism (5), an end of the mount cavity (31) is closed by the top cover (2), the top cover (2) is provided with a plug port (22) communicated with the mount cavity (31), and the atomization mechanism (5) comprises an atomization head (51) and a liquid storage bottle (52) connected to the atomization head (51);

the bracket (3) is provided with a positioning mechanism for positioning the atomization mechanism (5), and the positioning mechanism comprises a sliding member (8) for abutting against the atomization mechanism (5) and a positioning assembly (9) for positioning the sliding member (8), wherein the sliding member (8) is mounted slidably along the axial direction of the mount cavity (31) to the bracket (3), and the positioning assembly (9) comprises a door lock switch (91) and a buckle joint (93) that engages or disengages with the door lock switch (91) as the sliding member (8) moves up and down, and when the buckle joint (93) and the door lock switch (91) disengage, the atomization head (51) protrudes out of a mounting port;

an atomization cavity (511) is provided within the atomization head (51), the upper end of the atomization cavity (511) is provided with a fog hole (512) communicated with the outside of the atomization head (51), the inner wall of the atomization cavity (511) is respectively provided with a gas intake nozzle (514) communicated with the outside of the atomization head (51) and with a liquid intake nozzle (5153) communicated with the liquid storage bottle (52), and when the buckle joint (93) and the door lock switch (91) engage, the gas intake nozzle (514) is communicated with the gas supply assembly (6).

2. The fragrance atomization and diffusion device convenient for replacing a fragrance liquid container according to claim 1, wherein the sliding member (8) is provided in a circular shape, and there are at least two groups of the positioning assemblies (9) circumferentially arranged along the sliding member (8).

3. The fragrance atomization and diffusion device convenient for replacing a fragrance liquid container according to claim 1, wherein the positioning mechanism further comprises a limiting assembly (10) for limiting the sliding member (8), there are provided at least one group of the limiting assembly (10) and at least one group of the positioning assembly (9), each limiting assembly (10) corresponds to one positioning assembly (9), the limiting assembly (10) comprises a slider (101) and a sliding channel (102), the sliding channel (102) is provided along the sliding direction of the sliding member (8) with a sliding groove (1021), and the slider (101) is located within the sliding groove (1021) and slidably connected to the sliding groove (1021).

4. The fragrance atomization and diffusion device convenient for replacing a fragrance liquid container according to claim 1, wherein the positioning mechanism further comprises a resetting assembly (11) for driving the sliding member (8) to be reset, there are provided at least one group of the resetting assembly (11) and at least one group of the positioning assembly (9), each resetting assembly (11) corresponds to one positioning assembly (9), the resetting assembly (11) comprises a resetting spring (1101) for driving the sliding member (8) to move towards the opening direction of the mount cavity (31) and a guide rod (1102) fixedly connected to the bracket (3), and the resetting spring (1101) is sleeved on the guide rod (1102) and the upper end of the resetting spring abuts against the sliding member (8).

5. The fragrance atomization and diffusion device convenient for replacing a fragrance liquid container according to claim 1, wherein the atomization head (51) is provided along the radial direction thereof with at least one limit rib (517), the top cover (2) is provided at the opening of the mount cavity (31) with a limit rib groove (21) communicated with the upper end face of the top cover (2), the position and the number of which corresponds to those of the limit ribs (517), and when the limit rib (517) is located within the corresponding limit rib groove (21), the gas intake nozzle (514) is communicated with the gas supply assembly (6).

6. The fragrance atomization and diffusion device convenient for replacing a fragrance liquid container according to claim 1, wherein the gas supply assembly (6) comprises a gas pump (61) and a gas intake nozzle (62), and the gas pump (61) is communicated with the inner wall of the mount cavity (31) through the gas intake nozzle (62); the atomization head (51) is provided at the gas intake nozzle (514) with an insert groove (513) into which a connecting block (516) is inserted, and a communication cavity (5161) communicated with the gas intake nozzle (514) is provided within the connecting block (516); an end of the communication cavity (5161) far away from the gas intake nozzle (514) extends through the connecting block (516), and an end of the connecting block (516) towards the mount cavity (31) protrudes out of the side wall of the atomization head (51) and abuts against the inner wall of the mount cavity (31).

7. The fragrance atomization and diffusion device convenient for replacing a fragrance liquid container according to claim 6, wherein the inner wall of the mount cavity (31) is provided along the radial direction thereof with a limit groove (32), and the limit groove (32) extends along the sliding direction of the atomization head (51) to the opening of the top cover (2).

8. The fragrance atomization and diffusion device convenient for replacing a fragrance liquid container according to claim 7, wherein the connecting block (516) is made of elastic material and abuts against the limit groove (32).

9. The fragrance atomization and diffusion device convenient for replacing a fragrance liquid container according to claim 1, wherein the positioning assembly (9) further comprises a door lock mount block (92) detachably connected to the bracket (3) and provided along the thickness direction thereof with a mount groove (921), and the door lock switch (91) is inserted within the mount groove (921) and is limited and fixed along the length direction of the door lock switch (91).

10. The fragrance atomization and diffusion device convenient for replacing a fragrance liquid container according to claim 1, wherein the bracket (3) is provided with a mount base (33) having a bolt passed therethrough, the door lock mount block (92) is provided along the thickness direction thereof with a deform hole (923), and the bolt passes through the deform hole (923) and is threadedly connected to a side of the deform hole (923) far away from the mount base (33).

* * * * *